United States Patent [19]

Baak et al.

[11] 3,965,241

[45] June 22, 1976

[54] LEACHING TREMOLITE IMPURITY FROM TALC

[75] Inventors: N. Tryggve E. A. Baak, Marina Del Rey; Dwight L. Harris, Westlake Village, both of Calif.

[73] Assignee: Cyprus Mines Corporation, West Los Angeles, Calif.

[22] Filed: June 16, 1975

[21] Appl. No.: 587,175

[52] U.S. Cl. ............................. 423/155; 106/306; 423/331
[51] Int. Cl.² ...................................... C01B 33/24
[58] Field of Search .................. 423/155, 167, 331; 106/306; 241/4; 252/450

[56] References Cited
UNITED STATES PATENTS

| | | | |
|---|---|---|---|
| 1,598,256 | 8/1926 | Prutzman et al. | 252/450 |
| 2,576,653 | 11/1951 | Thomas | 252/450 |
| 3,116,974 | 1/1964 | Nikolai | 423/163 |
| 3,305,302 | 2/1967 | Heuer | 423/163 |
| 3,533,821 | 10/1970 | Lundquist | 106/306 |
| 3,806,043 | 4/1974 | Roe | 241/4 |
| 3,837,582 | 9/1974 | Baak | 241/4 |
| 3,932,194 | 1/1976 | Lamar | 106/306 |
| 3,939,249 | 2/1976 | Huege | 423/331 X |

OTHER PUBLICATIONS

Abido, "Chemical Abstracts," vol. 78, 1973, 87377k.

*Primary Examiner*—Edward J. Meros
*Attorney, Agent, or Firm*—Nilsson, Robbins, Dalgarn & Berliner

[57] ABSTRACT

A process for removing tremolite impurity from talc by subjecting finely ground talc to a combination of steps including froth flotation and pressure leaching with a strong acid at an elevated temperature. The recovered talc is characterized by a tremolite content of less than 1.0 percent by weight.

15 Claims, 1 Drawing Figure

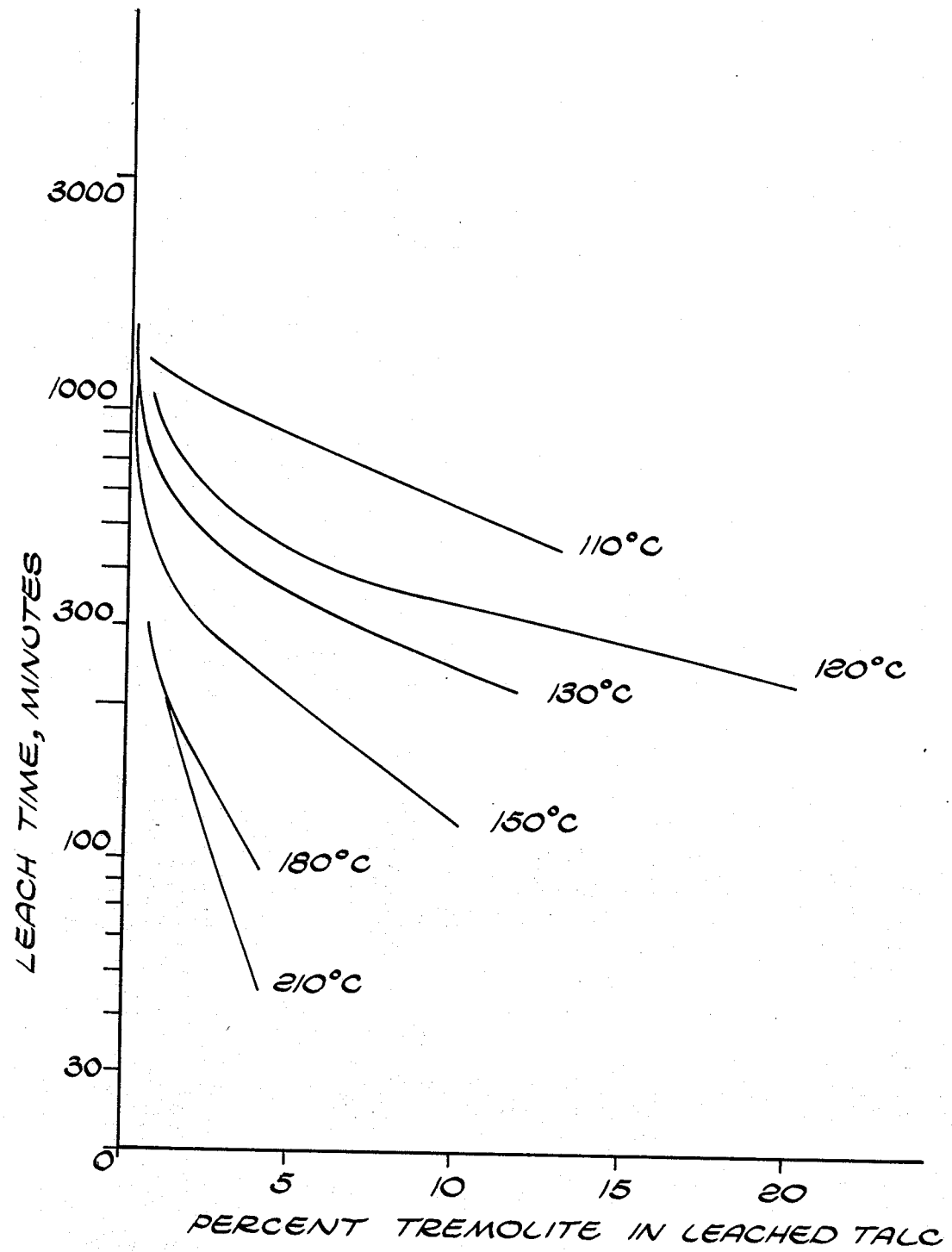

LEACHING TREMOLITE IMPURITY FROM TALC

BACKGROUND OF THE INVENTION

1. Field of the Invention

This invention relates to the production of a high purity talc from ore including a high proportion of undesirable impurities, such as asbestos in the form of tremolite.

2. Description of the Prior Art

High grade talc in the form of powder has found wide acceptance, for example as a grain coating agent, as a filler in paper, plastic and rubber, and in the cosmetics industry for application to human skin. For such uses, it is desirable to have the talc as free as possible of any irritating particles. In several instances, the use of talc as talcum-powder or as a grain coating agent has been pointed out as a health hazard when ingested or inhaled; however, it has been hypothesized that the impurity tremolite in the talc is the harmful agent. Tremolite is known as a potential occupational hazard. Tremolite, as well as other forms of asbestos, are described by the American Conference of Governmental Industrial Hygienists as occupational carcinogens. Accordingly, a process for removing tremolite from talc would be desirable. Certain talc ores, such as, for example, those found in the region of Gouverneur, New York and certain California talc ores, contain a substantial proportion of tremolite. Such ores would therefore benefit from an effective process for removing tremolite from talc.

Talc is hydrated magnesium silicate, $Mg_3[Si_4O_{10}](OH)_2$, a layer type lattice with relatively well satisfied valence bonds within the layer lattice and is relatively inert in many environments. Its platy, inert type of structure, has made it a safe, useful powder for dusting or coating surfaces. Tremolite, on the other hand, is a fibrous or bladed type of amphibole, having the formula $Ca_2Mg_5(Si_8O_{22})(OH)_2$, has less saturation of the surface bond, is more reactive, and has been a concern for health reasons, as pointed out above.

Many physical processes for separating talc from tremolite and other undesirable impurities, such as dolomite, calcite, quartz, chlorite, mica, etc. have been tried and have been effective, albeit in many cases costs of processing the ore have been high. Selective mining and/or hand sorting of lumps of ore which can be distinguished visually can be done and aids to visual sorting, such as fluorescent effects, have also been used. See, e.g., U.S. Pat. No. 3,837,582 to Baak. On the other hand, when the talc and the tremolite in the ores are very finely disseminated, physical separation processes are less effective and satisfactory amounts of tremolite are not removed.

It is known that leaching of talc with a strong acid, such as a mineral acid, can improve certain of its physical properties such as its brightness, wettability and surface area. See, e.g., U.S. Pat. No. 2,576,653 to Thomas which describes mineral acid treatment of a slurry of finely ground particles of a clay, such as talc, under broadly defined conditions which can include open vessel heating, refluxing, or heating in a closed vessel under steam pressure. Other patents which may be of some interest in this regard are U.S. Pat. No. 3,533,821 to Lundquist, U.S. Pat No. 3,271,323 to Whittmore, U.S. Pat. No. 2,574,895 to Stecker, U.S. Pat. Nos. 1,598,255 and 1,598,256, both to Prutzman et al, and U.S. Pat. No. 89,438 to Sell. While benefiting certain physical properties of talc, as described, none of the foregoing references report a decrease in tremolite, nor are they in fact particularly concerned with tremolite-containing talc.

SUMMARY OF THE INVENTION

It is a primary object of the present invention to provide an economical process for the production of a high purity talc from talc ore containing tremolite as an excessive impurity, i.e., greater than 1.0 percent tremolite.

The present invention is particularly suitable for the production of high quality talc from talc ores such, for example, as are found in the region of Gouverneur, N.Y., and in certain regions of California. By virtue of the present invention, a high quality talc product may be economically produced from such ores.

Generally stated, this invention provides a process for preparing a high quality talc ore containing tremolite as an excessive impurity by finely grinding the talc ore and subjecting the ground talc to a combination of steps including froth flotation and pressure leaching with a strong acid at an elevated temperature. Specifically, the talc is subjected to a temperature of at least 110°C and a pressure of at least 1.5 kg/cm² for a time sufficient to reduce the amount of tremolite to less than 1.0 weight percent of the talc, generally requiring at least 1 hour of pressure leaching.

While impurities other than tremolite, such as carbonates, can be removed effectively by acid-leaching talc in dilute or concentrated acids at temperatures from room temperature (for calcite) up to 80°C (for magnesite), the decomposition of tremolite in mineral acid does not occur appreciably until temperatures above 100°C and pressures above atmospheric are obtained. The rate of decomposition is dependant upon temperature and increases with temperature above the normal boiling point. The talc mineral is relatively unaffected in the range of temperature and pressure hereinafter described.

An essential feature of the present invention which is critical to the successful separation of the tremolite from the talc and the consequent production of a cosmetic grade product, is the combination of froth flotation and pressure-acid leaching operations. In this regard, it has been found that froth flotation alone will not afford a satisfactory separation of the tremolite impurities from the talc, nor will pressure acid leaching alone result in a satisfactory product. The froth flotation operation may be conducted before or after pressure acid leaching of the ground talc or may be conducted both before and after the leaching step. Each froth flotation may be conducted as a single step operation or, advantageously, the concentrate can be re-slurred for one or more successive operations.

The invention will be better understood when details thereof are considered in conjunction with the appended drawing.

BRIEF DESCRIPTION OF THE DRAWING

The FIGURE is a plot of tremolite content in talc versus pressure acid leach time for various temperatures in accordance with the present process.

DETAILED DESCRIPTION

Initially, the talc ore is crushed or ground to a particle size of minus 20 Tyler mesh, and preferably below minus 100 mesh, or finer. For cosmetic purposes, the ore should be ground to a particle size of 100 percent minus 100 mesh and 98 percent minus 200 mesh. Thereafter, the finely ground talc can be subjected directly to a pressure acid leaching process followed by a froth flotation operation in one or more steps with the concentrate washed, filtered and dried to yield the desired product. Alternatively, the finely ground talc can be initially subjected to a froth flotation operation in one or more steps with the concentrate subsequently combined with a strong acid and pressure leach. Since carbonates can be decreased by flotation prior to leaching, thereby minimizing acid requirements, initial flotation is preferred. Thereafter, the product can be directly washed, filtered and dried, or, if a product of extreme purity is desired, the leached concentrate can be again subjected to a froth flotation operation in one or more steps.

The pressure leach operation, whether directly on ground ore or on a flotation concentrate, is advantageously conducted in a closed vessel at steam pressure at the particular temperature selected. Such a vessel can be a Teflon-lined bomb of a size sufficient to hold the quantity of materials utilized. Alternatively, one could use any method for subjecting the slurry of talc and leaching acid to a suitable pressure.

In particular, the finely ground talc is slurried with a moderate aqueous solution of a strong acid, placed in a closable vessel, such as a bomb, whereupon the vessel is closed, heated to a temperature above 100°C, preferably to a temperature of at least 110°C. Although an upper temperature limitation is not as critical, there is no particular advantage in heating above 250°C and by operating within that range, one can avoid excessive decomposition of the talc. When using a closed vessel, and steam pressures generated thereby, the resultant pressures would be from 1.5 kg/cm$^2$ to 40 kg/cm$^2$. Pressures in excess of the foregoing can be applied from an external source, but are generally not required.

The pressure-acid leaching step is conducted for a time sufficient to reduce the amount of tremolite to less than 1.0 percent of the weight of the talc, as determined for a particular talc sample by analysis. Of course, higher temperatures and pressures generally require a shorter reaction time, but usually at least 1 hour. The pressure-acid leaching step can be conducted for extended periods of time if it is desired to reduce the level of tremolite to very small amounts, but, generally, heating for more than 5 days does not result in significant incremental decreases in tremolite content.

One can use any strong acid which results in a soluble reaction product, but which will not unduly attack the talc. In this regard, hydrofluoric acid would not be suitable as it will attack any silicate. Phosphoric acid can be used with talc containing small amounts of calcium carbonate, but with large amounts of calcium carbonate undesirable calcium by-products are formed which may be entrapped with the talc. While such strong organic acids such as perchloric acid and chloroacetic acid can be used, such are generally not economical for commercial processes. Accordingly, it is preferred to use a strong mineral acid such as hydrochloric acid, nitric acid and sulfuric acid, most preferably either hydrochloric acid or nitric acid. The use of sulfuric acid may result in a slow decrease in surface area over a long period of time, e.g. a year or more, and it may be hypothesized that carbon dioxide is entrapped in the surface of the talc leached with sulfuric acid. On the other hand, if such minor decreases in surface area are not of a major consideration, then sulfuric acid can be used.

Generally, a moderate acid concentration is used, between that which is considered a dilute solution and a strong solution. For example, with hydrochloric acid, usually supplied commercially in the range of 36–38 weight percent, an optimum solution would be obtained by diluting the acid with about an equal amount of water to obtain about 18–20 weight percent acid. Generally, at least 5 weight percent acid should be used and a concentration as high as 40 weight percent, or higher, can be used.

Froth flotation techniques for talc are well known, but in the present invention a preferred technique is to use a relatively dilute slurry, e.g., having a solids content of less than about 15 percent by weight, most preferably 10 percent or less by weight of the slurry, as described in Baak U.S. Pat. No. 3,837,582. Additionally, as known, a small amount of a water-soluble frother may be added, up to about 0.2 pounds of frother per ton of solids in the slurry, to improve separation of the talc from gangue material and to otherwise generally improve the froth flotation operation. Any well known commercially available frother may be used and particularly useful frothers are methyl isobutyl carbinol or isopropanol. Where isopropanol is used, it is generally desirable to add a small amount of sodium silicate to the slurry to further improve separation of talc. The slurry is then aerated and a first concentrate withdrawn. It has been found desirable to conduct the froth flotation in a series of steps whereby the concentrate from a prior step is reslurried and refloated, generally without addition of any reagents. A series of three flotation steps can be used to insure virtually complete removal of the tremolite and residues although a flotation operation incorporating two steps is generally sufficient to provide a talc product in which the tremolite content is less than 1%. The froths may be processed in a conventional manner by thickening, filtration, washing and drying.

An additional advantage of the process of the invention as described above is that fibrous magnesium silicates such as serpentine are also substantially reduced in content and for the most part removed with the tremolite. Furthermore, as an economic advantage, one can omit entirely the usual chlorine treatment, since the acid leach will remove all micro-organisms.

In order that those skilled in the art may better understand how the present invention may be practiced, the following examples are given by way of illustration and without limitation.

EXAMPLE I

A California talc ore containing about 15 percent tremolite and a small amount, several percent, of carbonates, is pulverized in a grinding mill to 100 percent minus 200 mesh. The sample is separately subjected to a froth flotation operation in which the talc ore is slurried with deionized water to make up a slurry of about 10 percent solids to which a drop of frother is added. The slurry is aerated and a concentrate obtained which is then washed, filtered and dried. Separate samples of the concentrate, each weighing 3 grams, are placed in Teflon-lined bombs with 10 milliliters of 18 weight percent hydrochloric acid. The bombs are closed and the slurries are heated in an electric oven at different temperatures and for different periods of time for various samples, from 110°up to 210°C for from 60 minutes to 1400 minutes. The pressures at which the samples are heated can be estimated from steam tables for water and are shown in the following table:

| Temperature | Absolute pressure, kg/cm² |
|---|---|
| 110°C | 1.5 |
| 120°C | 2.0 |
| 130°C | 2.7 |
| 150°C | 4.8 |
| 180°C | 10.2 |
| 210°C | 19.4 |

The tremolite content is determined on the washed residue from each test sample from X-ray diffraction patterns and X-ray spectrometry data.

Referring to the FIGURE, the tremolite content for various samples run at various temperatures is plotted with the analyzed amount of tremolite on the abscissa versus the pressure-acid leach time in minutes on the ordinate. The data shows that tremolite is effectively removed to a low level for each sample. Thus, for samples treated at 150°C, a tremolite content of substantially less than 1.0 percent is obtained after 500 minutes. For a sample treated at 130°C, a tremolite content of less than 0.3 percent is obtained after 1000 minutes of treatment. In each case, the talc content is found to be only slightly affected as confirmed by residue recoveries of 83 percent and higher.

EXAMPLE II

A New York talc ore is ground to a fine particle size and then screened through a 200 mesh screen. The oversized materials are repulverized and rescreened repeatedly to secure 100 percent minus 200 mesh materials as a flotation feed. A flotation pulp is prepared by slurrying the talc ore in deionized water to make up a slurry of 10% solids. To assure complete wetting, the pulp is mixed at a high speed for at least 30 minutes. Flotation consists of a 2 stage operation, i.e., rougher flotation and a cleaner flotation. Methyl isobutyl carbinol is added into the pulp just prior to the pumping of the pulp into the flotation cell at about 0.15 pounds per ton of solids in the slurry. The feed rate of the pulp to the rougher cell is about 45 pounds per hour. Following aeration, the concentrate is collected, re-slurried with deionized water to make a dilute pulp of about 10 percent solids and then is froth floated in the cleaner cell. The concentrate from the cleaner cell is then washed, filtered and dried and is found to contain about 1.5 weight percent tremolite.

Separate samples of the flotation concentrate are treated by a pressure-acid leaching bomb technique as in Example I under temperatures and pressure which vary from 110° to 160°C for time varying from 390 minutes to 4320 minutes as shown in the following table. The amounts of tremolite remaining in the treated samples are estimated by X-ray diffraction and are shown in the table.

| Sample | Time, min. | Temp., °C | % Tremolite in residue |
|---|---|---|---|
| 1 | 1110 | 110 | 0.75 |
| 2 | 4320 | 130 | 0.1 |
| 3 | 390 | 160 | 0.3 |
| 4 | 480 | 160 | 0.2 |

Sample number 2 shows the best elimination of tremolite by pressure-acid leaching for 72 hours at 130°C.

The present invention thus affords an improved process for economically producing high grade talc, such for example as may be used in cosmetic applications, from talc ore of the type mined in the Gouverneur, N.Y. region, or in certain regions of California, which type is characterized by relatively high contents of tremolite. The normal cosmetic grind of talc produced in accordance with the invention can be used as a dry lubricant of white color in place of graphite or molybdenum disulfide, both of which have adverse colors. In addition, talc produced by the process of the invention may also be used in the preparation of paint, paper, textiles, ceramic compositions, rubber, plastics, and various other applications by means well known to those skilled in the art.

It should be understood that while the present invention has been described in considerable detail with respect to certain specific embodiments thereof, it is not to be considered limited to those embodiments, but may be used in other ways without departure from the spirit of the invention or the scope of the appended claims.

What is claimed is:

1. A process for the preparation of high purity talc from talc ore containing tremolite as an impurity, which comprises:
   crushing said talc ore to provide finely ground talc of a particle size of minus 20 mesh;
   combining said finely ground talc with a strong acid;
   leaching said talc by subjecting said combination of talc and acid to a temperature of at least 110°C at a pressure of at least 1.5 kg/cm² for a time sufficient to reduce the amount of tremolite in said talc to less than 1.0 weight percent;
   prior or subsequent to said leaching step, forming a dilute aqueous slurry of said talc and subjecting said slurry to at least one froth flotation; and
   recovering a high purity talc.

2. The process of claim 1 in which said talc is crushed to provide a particle size of 100 percent minus 100 mesh and 98 percent minus 200 mesh.

3. The process of claim 1 in which said strong acid is a strong mineral acid.

4. The process of claim 3 in which said strong mineral acid is hydrochloric acid.

5. The process of claim 1 in which said temperature is in the range of 110°–250°C, said pressure is in a range of 1.5–40 kg/cm² and said leaching step is conducted for at least 1 hour.

6. A process for the preparation of a high purity talc from ore containing tremolite as an impurity, which comprises:
   crushing said talc ore to provide a finely ground talc of a particle size of minus 20 mesh;
   forming a dilute aqueous slurry of said crushed talc;
   subjecting said slurry to at least one froth flotation;
   removing the froth formed during the final froth flotation step to obtain a talc concentrate;
   combining said talc concentrate obtained from said final froth flotation with a strong acid;
   leaching said talc by subjecting said combination of talc concentrate and acid to a temperature of at least 110°C at a temperature of at least 1.5 kg/cm² for a time sufficient to reduce the amount of tremolite in said talc to less than 1.0 weight percent; and washing said leached talc and drying to recover a high purity talc.

7. The process of claim 6 in which said talc is crushed to provide a particle size of 100 percent minus 100 mesh and 98 percent minus 200 mesh.

8. The process of claim 6 in which said strong acid is a strong mineral acid.

9. The process of claim 8 in which said strong mineral acid is hydrochloric acid.

10. The process of claim 6 in which said temperature is in the range of 110°–250°C, said pressure is in the range of 1.5–40 kg/cm$^2$ and said leaching step is conducted for at least 1 hour.

11. A process for the preparation of a high purity talc from talc ore containing tremolite as an impurity, which comprises:

crushing said talc ore to provide finely ground talc of a particle size of minus 20 mesh;

combining said finely ground talc with a strong acid;

leaching said talc by subjecting said combination of talc and acid to a temperature of at least 110°C at a pressure of at least 1.5 kg/cm$^2$ for a time sufficient to reduce the amount of tremolite in said talc to less than 1.0 weight percent;

subsequent to said leaching step, forming a dilute aqueous slurry of said leached talc;

subjecting said slurry to at least one froth flotation;

removing the froth formed during the final froth flotation step; and recovering a high purity talc from said floated froth.

12. The process of claim 11 in which said talc is crushed to provide a particle size of 100 percent minus 100 mesh and 98 percent minus 200 mesh.

13. The process of claim 11 in which said strong acid is a strong mineral acid.

14. The process of claim 13 in which said strong mineral acid is hydrochloric acid.

15. The process of claim 11 in which said temperature is in the range of 110°–250°C, said pressure is in the range of 1.5–40 kg/cm$^2$ and said leaching step is conducted for at least 1 hour.

* * * * *

UNITED STATES PATENT AND TRADEMARK OFFICE
CERTIFICATE OF CORRECTION

PATENT NO. : 3,965,241
DATED : June 22, 1976
INVENTOR(S) : N. Tryggve E. A. Baak and Dwight L. Harris It is certified that error appears in the above-identified patent and that said Letters Patent are hereby corrected as shown below:

```
Col. 1, line 7, insert --talc-- before "ore".
Col. 2, line 19, insert --from talc-- before "ore".
```

Signed and Sealed this

Eleventh Day of January 1977

[SEAL]

Attest:

RUTH C. MASON
*Attesting Officer*

C. MARSHALL DANN
*Commissioner of Patents and Trademarks*